(12) United States Patent
Del Buono et al.

(10) Patent No.: US 7,776,839 B2
(45) Date of Patent: Aug. 17, 2010

(54) PHARMACEUTICAL COMPOSITIONS INCLUDING ALGINATES AND METHODS OF PREPARING AND USING SAME

(75) Inventors: Raffaele Del Buono, Harrow (GB); Peter William Dettmar, Patrington (GB); Frank Chadwick Hampson, Hedon (GB); Ian Gordon Jolliffe, Cottingham (GB); Paul Murray McPherson, Aberdour (GB); Edvar Onsoyen, Drammen (NO); Massimo Pignatelli, Bristol (GB); Peter Edward Ross, Broughty Ferry (GB)

(73) Assignee: Reckitt Benckiser Healthcare (UK) Limited (GB)

( * ) Notice: Subject to any disclaimer, the term of this patent is extended or adjusted under 35 U.S.C. 154(b) by 0 days.

(21) Appl. No.: 10/241,048

(22) Filed: Sep. 10, 2002

(65) Prior Publication Data

US 2003/0130229 A1 Jul. 10, 2003

Related U.S. Application Data

(63) Continuation of application No. PCT/GB01/01026, filed on Sep. 18, 2001.

(30) Foreign Application Priority Data

Mar. 10, 2000 (GB) ................................ 0005743.0

(51) Int. Cl.
*A51K 31/734* (2006.01)
(52) U.S. Cl. .......................................... 514/54; 514/23

(58) Field of Classification Search .................. 424/488, 424/489, 464, 439
See application file for complete search history.

(56) References Cited

U.S. PATENT DOCUMENTS

| | | | | |
|---|---|---|---|---|
| 5,266,326 A | * | 11/1993 | Barry et al. | 424/423 |
| 5,324,526 A | * | 6/1994 | Iwata et al. | 426/2 |
| 5,456,918 A | * | 10/1995 | Quirk et al. | 424/451 |
| 5,510,102 A | * | 4/1996 | Cochrum | 424/78.08 |
| 6,124,271 A | * | 9/2000 | Iversen et al. | 514/44 |

FOREIGN PATENT DOCUMENTS

| | | |
|---|---|---|
| GB | 1 524 740 | 9/1978 |
| GB | 2 093 697 A | 9/1982 |
| GB | 2 324 724 A | 11/1998 |
| GB | 2 324 725 A | 11/1998 |
| JP | 57 046920 A | 3/1982 |
| WO | WO 91/11205 A1 | 8/1991 |
| WO | WO 93/16111 A1 | 8/1993 |
| WO | WO 98/48814 A1 | 11/1998 |
| WO | WO 99/20318 A2 | 4/1999 |

* cited by examiner

*Primary Examiner*—Eric E. Silverman
(74) *Attorney, Agent, or Firm*—Troutman Sanders LLP; Ryan A. Schneider; Michael J. Brignati

(57) ABSTRACT

A pharmaceutical composition is provided for use in the healing of cells containing about 0.0001 percent weight per volume (% w/v) to about 2% w/v of an alginic acid or a salt of alginic acid having a molecular weight in the range of greater than about 250,000 to about 1,000,000, provided that if the composition additionally contains an alginic acid or a salt of alginic acid having a molecular weight in the range of about 20,000 to about 250,000, it is present in an amount of less than 1% w/w. The use of the pharmaceutical composition for the healing cells in a mammal, preferably mucosal cells is also provided.

12 Claims, 2 Drawing Sheets

Migration Dose Response - OE-33

Migration Dose Response - OE-33

Endocytosis Dose Response - OE21 H120L

PHARMACEUTICAL COMPOSITIONS INCLUDING ALGINATES AND METHODS OF PREPARING AND USING SAME

CROSS-REFERENCE TO RELATED APPLICATION

This is a continuation of PCT/GB01/01026, filed Mar. 9, 2001, which was published in the English language on Sep. 18, 2001 under International Publication No. WO 01/66119 A2, and the disclosure of which is incorporated herein by reference.

BACKGROUND OF THE INVENTION

This invention relates to a pharmaceutical composition for the treatment and/or prophylaxis of mucosal damage in a mammal. In particular, this invention relates to pharmaceutical compositions including water soluble salts of alginic acid.

The gastrointestinal (GI) tract in mammals consists of the oral cavity, the esophagus, the stomach and the small and large intestines. The tract is lined by a layer of cells known as the mucosa, which is stratified squamous non-keratinized epithelium in the case of the oral cavity and the esophagus and is columnar epithelium in the case of the stomach and intestines. This mucosa suffers a number of assaults from time to time, including:

mechanical damage and/or hot/cold stress from food and drink;

exposure to contents from the stomach and duodenum (reflux); and/or systemically and/or topically induced mucosal damage such as that caused by the action of prostaglandin inhibitors (aspirin) or indomethacin.

All of the above (but particularly reflux) can result in local injury to the mucosa which itself can lead to esophagitis (mucosal inflammation) and, in severe or chronic instances, Barrett's esophagus (in which a lower portion of the esophagus becomes lined with columnar epithelium).

The upper GI tract has many defense mechanisms which act to counter the assaults mentioned above. These include:

the secretion of mucus and bicarbonate which are generally considered to have both a protective and a neutralizing function;

the secretion of saliva which acts to lubricate the esophagus and raise the pH in the oral cavity and esophagus;

the lower esophageal or cardiac sphincter which acts to confine gastric contents to the stomach; and peristalsis or clearance whereby, through the action of swallowing, the bolus is moved through the esophagus to the stomach by peristaltic waves.

Often, however, these defenses prove inadequate and damage to the mucosa or cellular lining of the oral cavity, esophagus and/or stomach occurs. This damage is characterized by injury to the upper cell layers in the mucosa.

GB-A-2324725 discloses a pharmaceutical composition suitable for forming a mucoadhesive lining in the gastrointestinal tract which comprises an alginate or alginic acid having a mannuronic acid to guluronic acid residue ratio (M/G) of at least 1. The compositions disclosed comprise a combination of a low viscosity low molecular weight alginate and a high viscosity high molecular weight alginate.

GB-A-2324724 discloses a pharmaceutical composition comprising high concentrations (e.g. 8 to 15% w/w) of sodium alginate having an M/G ratio of at least 0.6:1.

EP-A-0059221 discloses a composition for the protection of the gastrointestinal tract which comprises a water soluble salt of alginic acid. The water soluble salt has a molecular weight of 60,000 to 250,000.

WO 91/11205 discloses a method of treating wounds comprising applying to a wound a biopolymer composition comprising at least 70% molar β-D-mannuronate. The specification proposes that the alginate biopolymers may be made into fibers and spun, woven, mixed or otherwise incorporated into wound dressings. For internal wounds, such as ulcers, the biopolymer is provided as a solution that will coat the walls of the gastrointestinal tract.

However, a need still exists for a pharmaceutical composition for use in the healing of mucosal damage in a mammal.

A further need exists for the manufacture of a pharmaceutical composition which provides for the healing of mucosal damage in a mammal.

BRIEF SUMMARY OF THE INVENTION

According to a first aspect of the present invention, there is provided a pharmaceutical composition for use in the healing of cells comprising about 0.0001 percent weight per volume (% w/v) to about 2% w/v of an alginic acid or a salt of alginic acid having a molecular weight in the range of greater than about 250,000 to about 1,000,000, provided that if the composition additionally contains an alginic acid or a salt of alginic acid having a molecular weight in the range of about 20,000 to about 250,000, it is present in an amount of less than about 1% w/v.

All references to molecular weight are weight average molecular weights (MW).

The applicants have surprisingly found that the amount of an alginic acid or an alginic acid salt as described, though significantly less than that taught to be effective in the prior art, is nonetheless effective in the healing of cells in a mammal, particularly mucosal cells.

In terms of the present invention, the term "mucosa" is intended to encompass the tissue layer found lining the GI tract of a mammal. As such, it is composed of a layer of epithelium containing numerous mucous glands and an underlying layer of areolar and lymphoid tissue.

The healing of cells contained in the mucosa is evidenced by the cells displaying one or more characteristics selected from:

endocytosis and/or ruffling;

a decrease in cell-cell adhesion;

an increase in cell motility, for example in wound restitution; and an epidermal growth factor (EGF) like response, for example, stimulation of the epidermal growth factor receptors (EGFr).

The present invention therefore provides a pharmaceutical composition as described for use in promoting any one or more of:

endocytosis and/or ruffling;

a decrease in cell-cell adhesion;

an increase in cell motility; and a stimulation of the epidermal growth factor receptors (EGFr) in a cell, preferably a mucosal cell.

Applicants have surprisingly discovered that high molecular weight alginic acids and alginic acid salts, particularly the water soluble salts, are more effective than low molecular weight alginic acids or alginic acid salts in promoting endocytic or/ruffling activity in cells, decreasing cell adhesion, increasing cell motility and/or mimicking the effect of epidermal growth factor by stimulating the EGFr on cells.

In addition, applicants have surprisingly discovered that, although lower molecular weight water soluble salts of alginic acid are not substantially effective in having a healing effect on cells, higher concentrations of these lower molecular weight salts do have this effect.

The alginic acids or alginic acid salts for use in the present invention are those having a molecular weight of greater than about 250,000 to about 1,000,000, more preferably about 300,000 to about 400,000. Water soluble salts are preferred. Examples of suitable grades of such water soluble salts of alginic acid are the sodium salts Protanal SF/LF, SF60L and H120L, all supplied by FMC Biopolymer a.s.

Another alginate which is particularly preferred is known as Poly M.

Alginic acid and alginates are linear hetero-polysaccharides comprising units of β-D-mannuronic acid (denominated M units) and ∝-L-mannuronic acid (denominated G units). Alginates, such as H120L, may be exposed to epimerases which cause the epimerization of some M units to G units. For example, H120L may be epimerized to H120LA, which is an alternase with alternating G units, or H120B, which is a blockase with blocks of G units, respectively.

Poly M may comprise about 95 to about 100% M units with an estimated molecular weight of up to about 1,000,000. Poly M may have a slight degree of epimerization which accounts for it having a less than 100% mannuronate content. Poly M may be degraded, for example by heating, to have a molecular weight of about 400,000.

The M/G ratio of the alginic acid or alginic acid salts used in the present invention is preferably at least about 1 and may be at least about 10 or above.

Relatively small amounts of the alginic acid or alginic acid salts are required in the present invention such that preferred concentrations are about 0.02 to about 1.8% w/v, more preferably about 0.05 to about 1.5% w/v.

However, in combination with the above, a lower molecular weight alginic acid or alginic acid salt may be used, but at a relatively higher concentration. Thus, an alginic acid or alginic acid salt having a molecular weight of about 20,000 to about 250,000 may be used at concentrations of about 2 to about 10% w/v, preferably about 2.5 to about 8% w/v.

Examples of suitable grades of the lower molecular weight water soluble salts of alginic acid are the sodium salts Protanal LFR5/60, SF120, LF10L and LF120 supplied by FMC Biopolymer a.s.

Mucosal damage may be systemically and/or topically induced, for example, by the consumption of prostaglandin inhibitors, such as acetyl salicylic acid (aspirin) or indomethacin, coupled with exposure to gastric contents, or the damage may be mechanically induced.

The damage may also be induced by the action of gastric contents on the esophageal mucosa through reflux of the luminal contents. The mucosal damage may be damage to any part of the epithelium of the gastrointestinal tract, including but not limited to the oral cavity, the esophagus and the stomach.

Previously, one approach to addressing the problem of reflux has been to administer a preparation which on contact with gastric acid generates a carbonated gelatinous foam or raft which floats on the stomach contents. When reflux occurs, it is this raft which precedes the stomach contents into the esophagus, thus protecting the mucosa from further irritation. Known preparations of this type include solid preparations in the form of powder or tablets containing a water soluble salt of alginic acid, sodium bicarbonate and antacid materials or liquid preparations containing sodium alginate, sodium bicarbonate and calcium carbonate marketed under the name GAVISCON® (Reckitt Benckiser plc).

Therefore, in one embodiment of the present invention, the compositions as described may be liquid, or become liquid upon vigorous shaking. Alternatively, the compositions may be presented as chewable tablets, granules, powders, soft gels and reconstitutable ~ liquids.

The inventors have found that through the use of the alginic acid or alginic acid salts of the invention, a pharmaceutical composition may be obtained which not only serves to physically prevent damage to the mucosa (as per GAVISCON®), but also has a healing effect on existing damage to the mucosa.

The invention includes a pharmaceutical composition, including what has previously been considered sub-clinical doses of selected forms of alginic acid or alginic acid salt, to exert a healing effect on the mucosa at a cellular level rather than presenting a physical barrier to reflux and/or having a coating effect (not unlike a conventional plaster dressing).

The water soluble salts of alginic acid may be sodium, potassium and/or magnesium salts. Preferably, however, the water soluble salt is sodium alginate. (The term "alginate" is intended to be used interchangeably with the term "alginic acid".)

Preferably, high viscosity grade sodium alginate is used to prepare the compositions. These are grades of sodium alginate for which the viscosity of an about 1% weight/volume aqueous solution, when determined on a Brookfield RVT viscometer using spindle number 3 at 20 r.p.m. at 20° C., falls within the range of about 200 to about 1500 mPa·s. An example of a suitable commercial grade of sodium alginate is Protanal H120L as supplied by FMC Biopolymer a.s.

The compositions may further comprise preservatives to prevent contamination and subsequent deterioration by micro-organisms. Examples of suitable preservatives are methyl, ethyl, propyl and butyl para-hydroxybenzoates and their salts, which are preferably used in combination, e.g. methyl and propyl or ethyl and butyl.

Preferred concentrations for the preservatives are about 0.01 to about 0.5% w/v.

The compositions may also include one or more of the following ingredients: thickeners, suspending agents, tabletting agents, glidants, diluents, coloring, sweetening, flavoring or pH adjusting ingredients.

According to a second aspect of the present invention, there is provided a pharmaceutical composition comprising about 0.0001 percent weight per volume (% w/v) to about 2% w/v of alginic acid or a salt of alginic acid having a molecular weight in the range of above 250,000 to about 1,000,000 for use in the healing of cells in a mammal, as evidenced by the promotion of one or more selected from the group consisting of:

endocytosis and/or ruffling;

a decrease in cell-cell adhesion;

an increase in cell motility; and a stimulation of the EGF receptors (EGFr) in a cell, provided that if the composition additionally contains an alginic acid or a salt of alginic acid having a molecular weight in the range of about 20,000 to about 250,000, it is contained in an amount of less than about 1% w/v.

The treatment may comprise administering to a mammal in need thereof, a therapeutically effective amount of the composition. A therapeutically effective amount of the composition may present about 0.1 to about 50 mg of the alginic acid salt per kilogram of the mammal, preferably about 1 to about 10 mg/kg. Such dosages may be repeated about every 4 to about 24 hours.

According to a further aspect to the present invention there is provided a process for the preparation of pharmaceutical compositions comprising about 0.0001 percent weight per volume (% w/v) to about 2% w/v of alginic acid or a salt of alginic acid having a molecular weight of greater than about 250,000 to about 1,000,000 and a pharmaceutically acceptable carrier, the process including the steps of adding the alginic acid or alginic acid salt to the carrier and mixing.

According to a further aspect of the invention, there is provided a method for the healing of cells in a mammal, the method comprising the steps of administering to a mammal in need thereof a pharmaceutically effective amount of a pharmaceutical composition comprising about 0.0001 percent weight for volume (% w/v) to about 2% w/v of alginic acid or a salt of alginic acid having a molecular weight in the range of about 250,000 to about 1,000,000.

The pharmaceutical composition which is administered to a mammal promotes any one or more selected from the group consisting of:
  endocytosis and/or ruffling;
  a decrease in cell-cell adhesion;
  an increase in cell motility; and
  a stimulation of the epidermal growth factor receptors (EGFr) in a cell, preferably a mucosal cell.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1A:
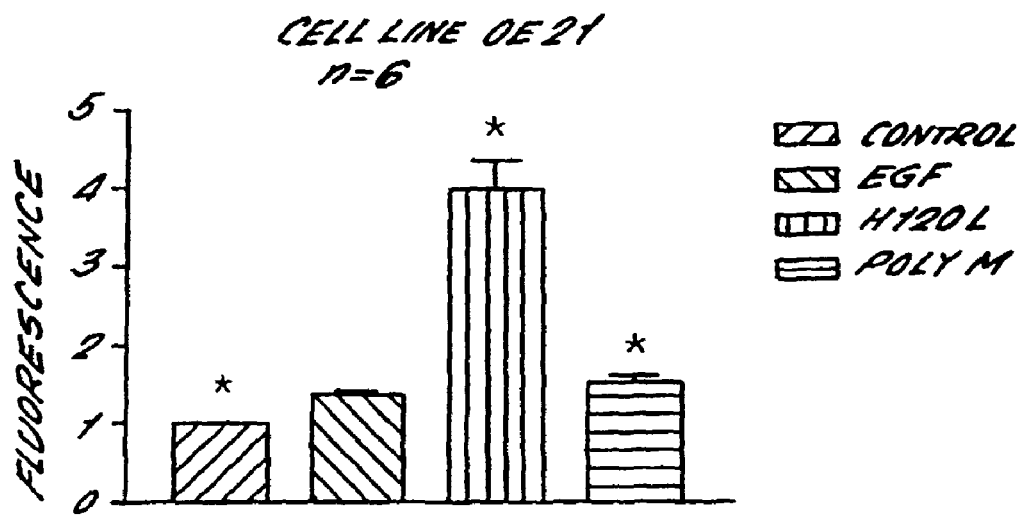
FIG. 1A illustrates the results of the effect of certain alginates (2 mg/ml) in promoting endocytosis in squamosa carcinoma cells (OE21)

The invention will now be described with reference to the following examples.

EXAMPLE 1

Indomethacin-Induced Mucosal Damage in Rats

Alginates Protanal H120L, LFR5/60 and LF10L (supplied by FMC Biopolymer a.s.) were used in the study.

The different samples of alginate (4 mg/ml in $H_2O$ containing 2% w/v hydroxypropylmethyl cellulose (HPMC)) were administered by gastric gavage to rats (2 ml per rat).

2% w/v HPMC in $H_2O$ was administered by gastric gavage as the negative control.

50 µg/kg Epidermal Growth Factor (EGF) in $H_2O$ containing 2% w/v HPMC was administered by gastric gavage as the positive control.

After 30 minutes, all rats were subcutaneously injected with 20 mg/kg indomethacin (20 mg/ml indomethacin in 5% w/v sodium bicarbonate). The rats were then restrained in Bollman cages.

Three hours later, the rats were sacrificed, their stomachs removed and fixed in formalin overnight. Damage to the gastric mucosa was assessed macroscopically by opening the stomachs and pinning them out, then placing a transparent sheet with a 1 mm grid placed on top and thereafter assessing the total area of macroscopic damage.

The results were as follows:

TABLE 1

Results of macroscopic gastric mucosal damage in rats.

| Substance | 2% HPMC | EGF | H120L | LFR5/60 | LF10L |
|---|---|---|---|---|---|
| Gastric Damage ($mm^2$) (n = 5) | 51.00 | 30.00 | 24.00 | 75.00 | 47.00 |
|  | 40.00 | 7.00 | 27.00 | 77.00 | 47.00 |
|  | 46.00 | 37.00 | 12.00 | 36.00 | 40.00 |
|  | 57.00 | 13.00 | 17.00 | 37.00 | 32.00 |
|  | 91.00 | 34.00 | 36.00 | 50.00 | 58.00 |
| Average | 57.00 | 24.20 | 23.20 | 55.00 | 44.80 |
| Standard Deviation | 20.01 | 12.14 | 8.46 | 19.96 | 9.62 |

From these results, it can be seen that alginate H120L significantly outperforms in ameliorating gastric mucosal damage in rats having gastric mucosal damage systemically induced by indomethacin.

EXAMPLE 2

Indomethacin-Induced Mucosal Damage in Rats (Second Study)

The same protocol as for Example 1 was used, but the following alginate/control solutions were administered to the rats (all weights per volume):
  2% HPMC
  2% HPMC+50 µg/kg EGF
  50 µg/kg EGF
  4 mg/ml H120L+2% HPMC
  4 mg/ml H120L
  4 mg/ml H120L(a) (autoclaved)

The results were as follows:

TABLE 2

Results of macroscopic gastric mucosal damage in rats.

| Substance | 2% HPMC | HPMC + EGF | EGF | H120L + HPMC | H120L | H120L(a) |
|---|---|---|---|---|---|---|
| Gastric Damage ($mm^2$) (n = 5) | 64.00 | 25.00 | 15.00 | 27.00 | 46.00 | 56.00 |
|  | 74.00 | 26.00 | 14.00 | 37.00 | 29.00 | 33.00 |
|  | 59.00 | 27.00 | 28.00 | 29.00 | 37.00 | 62.00 |
|  | 77.00 | 21.00 | 14.00 | 32.00 | 33.00 | 50.00 |
|  | 57.00 | 27.00 | 17.00 | 33.00 | 30.00 | 50.00 |

TABLE 2-continued

Results of macroscopic gastric mucosal damage in rats.

| Substance | 2% HPMC | HPMC + EGF | EGF | H120L + HPMC | H120L | H120L(a) |
|---|---|---|---|---|---|---|
| Average | 66.20 | 25.20 | 17.60 | 31.60 | 35.00 | 50.20 |
| Standard Deviation | 8.93 | 2.49 | 5.94 | 3.85 | 6.89 | 10.83 |

These results show the effect of H120L is similar to the effects of EGF in protecting GI mucosa in rats. The HPMC solution has no effect, and the effect of H120L is significantly reduced when the structure is broken down by autoclaving (H120L(a)).

EXAMPLE 3

Cell Migration

A cell culture insert crucible having an 8 μm millipore filter is suspended in each of the following test substances:
H120L (1 mg/ml);
epidermal growth factor (EGF) ($10^{-8}$ M);
OE33 esophageal EGFr negative cells were added to the crucible and left for three hours.

After this time, the number of cells having moved through the filter into the test substance was estimated using bound dye technique (toluidine blue) via colorimetric assay. The results are as follows:

TABLE 3

Cell Migration Assay

| Test Substance | Migration |
|---|---|
| Control | 1.8 |
| H120L | 14.5 |
| EGF | 10.0 |

These results indicate that H120L has an increased effect on cell migration over and above the known effect of epidermal growth factor. Thus, H120L would be expected to have a correspondingly negative affect on cell-cell adhesion and a positive effect on wound restitution.

EXAMPLE 4

Using the technique as described in Example 3, the following test substances (all at 1 mg/ml):
Epidermal growth factor (EGF)
H120L
LFR 5/60
Poly M
Poly M (degraded)
H120L-A
H120L-B
were tested against the following cell lines:
AGS (gastric)
MKN (gastric)
OE-33 (esophageal)
KYSE-30 (esophageal)

The results are given in Table 4 below, expressed as the percentage specific migration above that of the control.

TABLE 4

Cell Migration Assays.

| Cell Lines | EGF | H120L | LFR 5/60 | Poly M | Poly M Deg | H120L-A | H120L-B |
|---|---|---|---|---|---|---|---|
| AGS | 61.1% | 226.7% | 66.6% | 235.5% | 70% | 118.9% | 0% |
| MKN-45 | 272.7% | 235.8% | 153.4% | 199.5% | 119% | 1.9% | 63.5% |
| OE-33 | 94.78% | 210.21% | 86.76% | 105.35% | 86.76% | 77.04% | 44.96% |
| KYSE-30 | 0% | 39.43% | 0% | 0% | 44.74% | 0% | 0% |

EXAMPLE 5

Endocytosis

A cell line of HCT116 cells was seeded out onto wells the night before the experiment. The cells were incubated for one hour with the alginic acid samples at 0.2 mg/ml and 2 mg/ml. Molecular probes (Fluorospheres®) in the form of polystyrene microspheres were used as a fluorescent marker, and the fluorescence in the cells was analyzed by flow cytometry.

In addition to the above, porcine esophagus biopsies were incubated in Ussing chambers and analyzed as above.

The results are as follows (corrected for a normal value of 1.0):

TABLE 5

Endocytosis Assay

| | HCT116 Cells | | Ussing Chambers | |
|---|---|---|---|---|
| Alginate | 0.2 mg/ml | 2.0 mg/ml | 0.2 mg/ml | 2.0 mg/ml |
| LF10L | 105 | 130 | 123 | 122 |
| LFR5/60 | 126 | 156 | 91 | 113 |
| SF120 | 102 | 166 | 106 | 96 |
| LF120L | 102 | 124 | 76 | 118 |
| SF60L | 92 | 153 | 135 | 77 |
| SF/LF | 115 | 175 | 169 | 89 |
| H120L | 100 | 248 | 93 | 170 |
| SF200 | 90.5 | 154 | 74 | 79 |
| UPLVG | 112 | 202 | 93 | 90 |
| Xanthan | 120 | 212 | 94 | 63 |

These results clearly indicate that alginates have a positive effect in promoting endocytosis in GI cells in a mammal.

EXAMPLE 6

Cell lines of OE21 squamosa carcinoma cells and of DE33 adenocarcinoma cells were seeded out into wells two days before the experiment. The cells were incubated for one hour with various alginate samples at concentrations of 2 mg/ml and epidermal growth factor at a concentration of 10 mg/ml. Molecular probes (Fluorospheres®) in the form of polystyrene microspheres were used as a fluorescent marker, and the fluorescence in the cells was analyzed by flow cytometry.

The following alginates were tested in this experiment.

H120L

Poly M

Figure 1B:
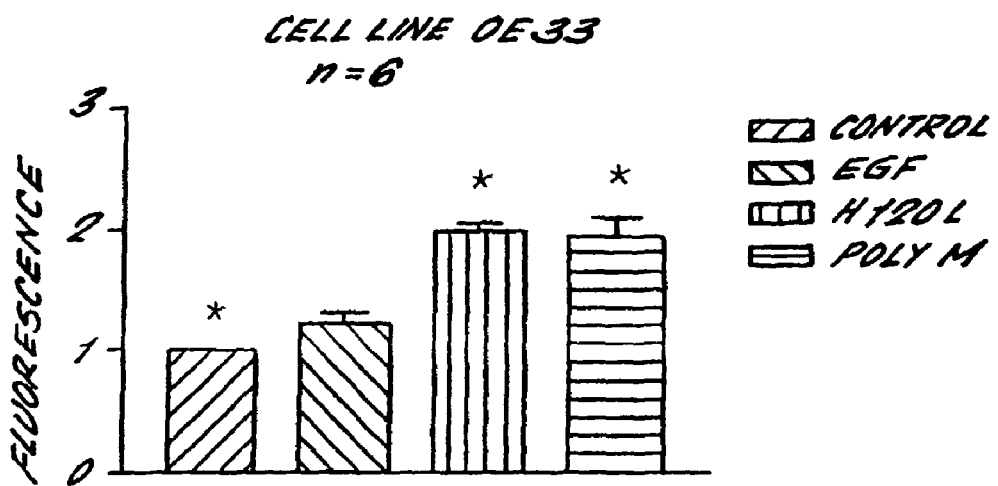
FIG. 1B illustrates the results of the effect of certain alginates (2 mg/ml) in promoting endocytosis in adenocarcinoma cells (OE33).
Figure 2:
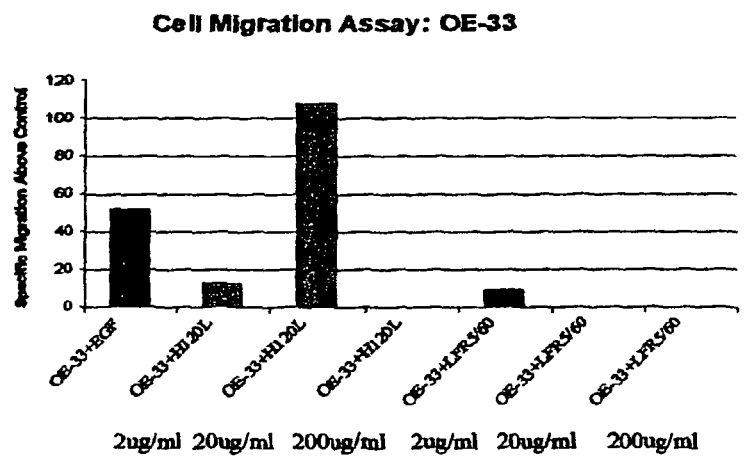
FIG. 2 illustrates the migration dose response of OE33 cell lines in different concentrations of H120L and LFR5/60. It can clearly be seen from this illustration that lower molecular weight alginates, such as LFR5/60, do not have an appreciable effect on cell migration at low concentrations, whereas higher molecular weight alginates, such as H120L, do have an effect at these lower concentrations.
Figure 3:
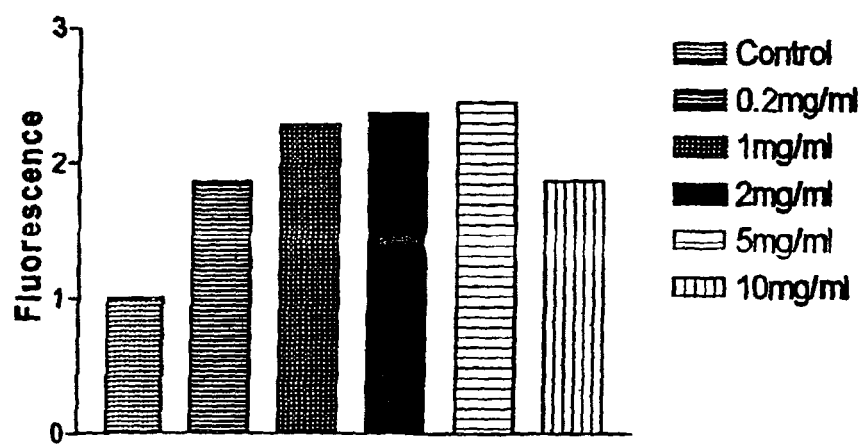
FIG. 3 illustrates the endocytosis dose response of OE21 cell lines in response to differing concentrations of H120L. It can be seen from this illustration that there is a maximum effect at 5 mg/ml H120L.

The results are shown in FIGS. 1A and 1B. These results indicate a significant increase in endocytosis in the presence of these alginates.

EXAMPLE 7

Binding to Epidermal Growth Factor Receptors

Esophageal squamous carcinoma cells (Cell line OE33) were incubated for one hour with different alginate grades- SF60L, H120L, SF/LF and LFR5/60. The alginate was then removed and epidermal growth factor added. Fluorescent epidermal growth factor and CT-b FITC or transferring were added to the cell culture dish at the same time and incubated for one hour at 37° C. with 5% $CO_2$.

Confocal microscopy and flow cytometry were used to analyze the results. Observations indicated that when the cells were incubated with the alginates, there was no evidence of epidermal growth factor binding to epidermal growth factor receptors. This indicates that the alginates seem to mimic the effect of epidermal growth factor on a cell in that the alginates seem to bind to the epidermal growth factor receptors on the cell membrane.

EXAMPLE 8

Aqueous Liquid Compositions

I. A composition containing:

| | | |
|---|---|---|
| Sodium Alginate H120L | 0.4% | w/v |
| Sodium Ethyl parahydroxybenzoate | 2.0% | w/v |
| Sodium Butyl parahydroxybenzoate | 0.2% | w/v |
| Sweetener | q.s. | |
| Flavor | q.s. | |
| Deionized water | to 100% | | was prepared according to the following instructions:
1. Dissolve the preservatives, flavor and sweetener.
2. Add the alginate and stir to dissolve.
3. Add water to 100%.

II. A liquid composition was prepared as above, but with the addition of 2% w/v hydroxypropylmethyl cellulose (2% solution with a viscosity of 100 mPa·s.−1 at 25° C.) added at stage 1.

III. A buffered solution containing the following was prepared:

| | |
|---|---|
| Sodium Alginate H120L | 0.6% w/v |
| Hydroxy Propyl Methyl Cellulose | 2.0% w/v |
| Monopotassium Phosphate | 0.02% w/v |
| Dipotassium Phosphate | 0.04% w/v |
| Sodium Ethyl parahydroxybenzoate | 2.0% w/v |
| Sodium Butyl parahydroxybenzoate | 0.2% w/v |
| Sweetener | q.s. |
| Flavor | q.s. |
| Deionized water | to 100% |

IV. The buffered solution with an antacid component was prepared as in III, but sodium bicarbonate and calcium carbonate were added, both 2.0% w/v.

EXAMPLE 9

Bioadhesive Liquids

Bioadhesive liquids containing the following were prepared:

| | mg/10 ml |
|---|---|
| I. | |
| Monopotassium phosphate | 20.00 |
| Dipotassium phosphate | 40.00 |
| Sodium bicarbonate | 168.00 |
| Ethyl paraben | 20.00 |
| Sodium butyl paraben | 2.22 |
| Sodium saccharin | 10.00 |
| Xanthan gum | 49.00 |
| Calcium carbonate | 80.00 |
| Locust bean gum | 21.00 |
| Sodium alginate H120L | 4.00 |
| Flavor | 7.00 |
| Deionized water | to 10 ml |
| II. | |
| Monopotassium phosphate | 20.00 |
| Dipotassium phosphate | 40.00 |
| Sodium bicarbonate | 168.00 |
| Ethyl paraben | 20.00 |
| Sodium butyl paraben | 2.22 |
| Sodium saccharin | 10.00 |
| Xanthan gum | 49.00 |
| Calcium carbonate | 80.00 |
| Locust bean gum | 21.00 |
| Sodium alginate H120L | 4.00 |
| Sodium Alginate LFR5/60 | 550.00 |
| Flavor | 7.00 |
| Deionized water | to 10 ml |

EXAMPLE 10

Powders

A dry powder mixture in sachet for dissolving in water prior to administration containing:

| | |
|---|---|
| Sodium Alginate H120L | 0.2 g |
| Sucrose | 4.8 g |
| Flavor | 0.1 g |
| Sweeteners | 0.1 g per sachet | was prepared according to the following instructions:

-continued

1. Dry blend and fill into sachets.
2. Reconstitute by pouring sachet contents into 100 ml water.
3. Stir to dissolve.

EXAMPLE 11

Chewable Tablet

A chewable tablet containing:

| | | |
|---|---|---|
| 1. | Alginate H120L | 5 mg |
| 2. | Xylitol | 1000 mg |
| 3. | Mannitol | 1350 mg |
| 4. | Povidone K30 | 50 mg |
| 5. | Flavor | 25 mg |
| 6. | Magnesium stearate | 25 mg | was prepared according to the following instructions:
1. Dryblend 1, 2 and 3.
2. Granulate using a solution of 4 in isopropanol, dry at 50° C.
3. Pass through a 1000 micron mesh.
4. Add 5 and 6 to the granules, mix for 3 minutes and press into tablets.

Upon chewing, the combination with approximately 10 ml of saliva gives a 0.05% w/v active alginate solution.

EXAMPLE 12

Oral Gel

An oral gel containing the following was prepared:

| | | |
|---|---|---|
| Alginate H120L | 0.4% | w/v |
| Hydroxy Propyl Methyl Cellulose | 10.0% | w/v |
| Sodium Ethyl parahydroxybenzoate | 0.2% | w/v |
| Sodium Butyl parahydroxybenzoate | 0.2% | w/v |
| Flavor | q.s. | |
| Sweetener | q.s. | |
| Water | to 100% | |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for healing mucosal cells lining the gastrointestinal tract of a mammal, the method comprising the step of orally administering to a mammal in need thereof a pharmaceutically effective amount of a pharmaceutical composition comprising a drug, wherein the drug consists of from 0.0001 percent weight per volume (% w/v) to 2% w/v of alginic acid or a salt of alginic acid having a molecular weight in a range of from greater than 250,000 to 1,000,000.

2. The method according to claim 1, in which the pharmaceutical composition further comprises at least one member selected from the group consisting of thickeners, suspending agents, tabletting agents, glidants, diluents, coloring ingredients, sweetening ingredients, flavoring ingredients, pH adjusting ingredients, and preservatives selected from the group consisting of methyl-, ethyl-, propyl- and butyl-parahydroxybenzoates, their salts and mixtures thereof.

3. The method according to claim 1, wherein the pharmaceutical composition is in a form selected from the group consisting of a liquid, a chewable tablet, a granule, a powder, and a soft gel.

4. A method for promoting endocytosis and/or ruffling in mucosal cells lining the gastrointestinal tract of a mammal, which comprises the step of orally administering to the mammal a pharmaceutically effective amount of a pharmaceutical composition comprising a drug, wherein the drug consists of from 0.0001 percent weight per volume (% w/v) to 2% w/v of alginic acid or a salt of alginic acid having a molecular weight in a range of from greater than 250,000 to 1,000,000.

5. A method for decreasing cell-cell adhesion in mucosal cells lining the gastrointestinal tract of a mammal, which comprises the step of orally administering to the mammal a pharmaceutically effective amount of a pharmaceutical composition comprising a drug, wherein the drug consists of from 0.0001 percent weight per volume (% w/v) to 2% w/v of alginic acid or a salt of alginic acid having a molecular weight in a range of from greater than 250,000 to 1,000,000.

6. A method increasing the motility of mucosal cells lining the gastrointestinal tract of a mammal, which comprises the step of orally administering to the mammal a pharmaceutically effective amount of a pharmaceutical composition comprising a drug, wherein the drug consists of from 0.0001 percent weight per volume (% w/v) to 2% w/v of alginic acid or a salt of alginic acid having a molecular weight in a range of from greater than 250,000 to 1,000,000.

7. A method for stimulating epidermal growth factor receptors in mucosal cells lining the gastrointestinal tract of a mammal, which comprises the step of orally administering to the mammal a pharmaceutically effective amount of a pharmaceutical composition comprising a drug, wherein the drug consists of from about 0.0001 percent weight per volume (% w/v) to 2% w/v of alginic acid or a salt of alginic acid having a molecular weight in a range of from greater than 250,000 to 1,000,000.

8. The method according to any of claim 1, 4, 5, 6 or 7 in which the pharmaceutical composition further comprises from about 2% w/v to about 10% w/v of alginic acid or a salt of alginic acid having a molecular weight in a range of from 20,000 to 250,000.

9. The method according to any of claim 1, 4, 5, 6 or 7, wherein the alginic acid or alginic acid salt has a molecular weight of from about 300,000 to about 400,000, and is present in the pharmaceutical composition in an amount of from about 0.02% w/v to about 1.8% w/v.

10. The method according to any of claim 1, 4, 5, 6 or 7, wherein the alginic acid or alginic acid salt has a mannuronic acid residue to guluronic acid residue ratio (M/G) of at least about 1.

11. The method according to claim 10, wherein the M/G ratio is at least about 10.

12. The method according to any of claim 1, 4, 5, 6 or 7, wherein the salt of alginic acid is a water soluble salt in which at least one member is selected from the group consisting of sodium, potassium and magnesium salts.

* * * * *